(12) United States Patent
Henley et al.

(10) Patent No.: US 8,114,663 B1
(45) Date of Patent: Feb. 14, 2012

(54) METHOD FOR CONSOLIDATED WASTE MANAGEMENT AND RESOURCE RECOVERY

(75) Inventors: Michael V. Henley, Panama City, FL (US); Lixiong Li, Panama City, FL (US); Theodore V. Marolla, Panama City, FL (US); William Wallace, Panama City, FL (US); Seth M. Foulkes, Johnstown, PA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 12/623,674

(22) Filed: Nov. 23, 2009

(51) Int. Cl.
*C12M 1/00* (2006.01)
*C12M 3/00* (2006.01)

(52) U.S. Cl. ............ 435/289.1; 435/262; 210/603

(58) Field of Classification Search ............ 435/157, 435/167, 168, 289.1, 262, 299.1, 300.1; 252/373; 585/240; 210/603
See application file for complete search history.

(56) References Cited

U.S. PATENT DOCUMENTS

| 2004/0023086 A1* | 2/2004 | Su et al. ............ 429/17 |
| 2004/0079087 A1* | 4/2004 | Chandran et al. ........ 60/781 |
| 2008/0045762 A1* | 2/2008 | Foody et al. .......... 585/240 |

\* cited by examiner

*Primary Examiner* — Michael Marcheschi
*Assistant Examiner* — Shanta G Doe
(74) *Attorney, Agent, or Firm* — Fredric Sinder; AFMCLO/JAZ

(57) ABSTRACT

A waste management and resource recovery system that uses the different waste streams from typical waste sources as fuel or feedstock for its subsystems that, in turn, produce fuel, feedstock or energy for other subsystems such that all the different waste streams are effectively managed. The subsystems include a gas burner for solid and fuel wastes that supplies heat to a hydrothermal processor for saccharification of paper and cardboard. The resulting saccharification broth, along with kitchen wastes and blackwater, are supplied to a bioreactor using dark fermentation to produce hydrogen and volatile fatty acids. The hydrogen and volatile fatty acids are supplied to hydrogen and microbial fuel cells to produce electrical energy for operating the system and potable water. A steam accumulator is added to provide sufficient temperatures and pressures to reach the necessary thermodynamic states for the saccharification process. An enzymatic saccharification processor may also improve the saccharification process.

2 Claims, 2 Drawing Sheets

METHOD FOR CONSOLIDATED WASTE MANAGEMENT AND RESOURCE RECOVERY

RIGHTS OF THE GOVERNMENT

The invention described herein may be manufactured and used by or for the Government of the United States for all governmental purposes without the payment of any royalty.

BACKGROUND OF THE INVENTION

The present invention relates generally to waste management systems, and more particularly to an integrated waste management and resource recovery system for handling the entire waste output of a large facility such as a deployed air or other military base.

Deployed airbases are essential platforms for the U.S. Air Force to launch weapon systems at overseas locations. The Army and other military departments have a similar need for deployed bases, sometimes referred to as Bare Bases.

To sustain these deployed military bases, particularly over long durations, a large number of ground personnel are required to provide support for operational and base activities, inevitably generating significant amounts of wastes on a daily basis. According to a study on deployable waste management systems, more than 196,000 lbs/day of solid and liquid wastes and wastewater are generated at a typical 1,100-person Bare Base.

Typical wastes include significant amounts of blackwater (wastewater from toilets), graywater (wastewater from other than toilets), food waste, solid wastes such as wood and cardboard, medical wastes and waste oils. Traditionally, blackwater and solid waste are trucked off site by local contractors, an onsite incinerator is used to treat medical waste, and an onsite lagoon is constructed and maintained to treat graywater (primarily by solar evaporation).

This traditional waste and resource management approach is not only a logistical burden, but using local contractors and truck convoys are significant security issues, particularly from contractor personnel coming on base to haul waste.

At the same time, essential materials, particularly water, must be supplied in large quantities on a daily basis. Water is an essential and high-volume logistical material for military operations involving long duration human settlement in isolated areas, where self-sufficiency is required to minimize logistic burdens of nonweaponry supplies. Also, wastewaters generated from living quarters must be effectively managed to maintain sanitary conditions for operational personnel.

Of all innovative technologies emerging within the Bare Base environment, waste management remains the least developed.

Developing a self-contained system that effectively handles the waste from a deployed military base will enhance environmental stewardship, reduce the environmental impact on a host nation and increase security.

Similar self-contained systems will also find great use after disasters such as floods and hurricanes.

Thus it is seen that there is a need for an effective and deployable waste management and resource recovery systems to enhance force protection, improve sanitary conditions and reduce logistic burdens.

SUMMARY OF THE INVENTION

The present invention provides a new integrated material and energy management system to recycle wastes and wastewaters generated from human activities that maximizing synergies among selected component technologies to achieve system versatility, deployability and robustness.

The invention is directed to a waste management and resource recovery system comprising a plurality of subsystems, wherein at least part of the output of each of a subplurality of the subsystems is supplied to at least one other subsystem as an input to that other subsystem; and wherein the subsystems include a burner; a hydrothermal processor assembly; a bioreactor assembly and a fuel cell assembly, and further including a steam accumulator for supplying steam to the hydrothermal processor assembly.

The invention is also directed to a waste management and resource recovery system, comprising a plurality of subsystems, wherein at least part of the output of each of a subplurality of the subsystems is supplied to at least one other subsystem as an input to that other subsystem, and wherein the subsystems include a burner, a hydrothermal saccharification processor, an enzymatic saccharification processor, a bioreactor assembly and a fuel cell assembly.

DETAILED DESCRIPTION

Figure 1:
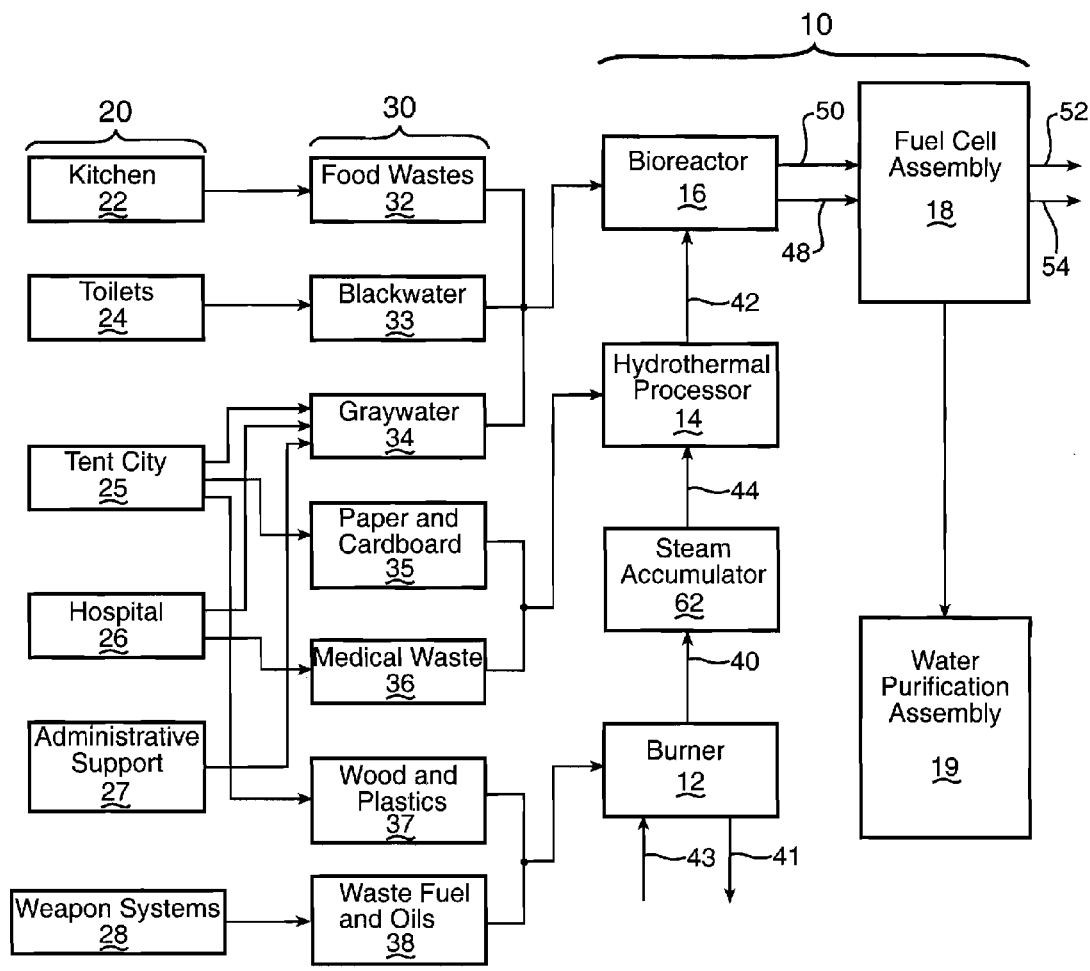
FIG. 1 is an example embodiment of a waste management and resource recovery system according to the teachings of the present invention showing the processing of typical wastes from a deployed airbase.

FIG. 1 is an example embodiment of a waste management and resource recovery system 10 showing the processing of typical wastes from a deployed airbase. The primary components of system 10 are a burner 12, a hydrothermal processor 14, a bioreactor 16, a fuel cell assembly 18 and a water purification assembly 19.

Example waste sources 20 include a kitchen 22, toilets 24, a tent city 25, a hospital 26, administration support 27 and weapon systems 28.

Example wastes 30 from waste sources 20 include food wastes 32, blackwater 33, graywater 34, paper and cardboard 35, medical wastes 36, wood and plastics 37 and waste fuel and oils 38.

The primary function of hydrothermal processor 14 is saccharification, the process of breaking down a complex carbohydrate, such as starch or cellulose, into its monosaccharide components, such as simple sugars, using hydrolysis.

The primary function of bioreactor 16 is dark fermentation, fermentative conversion of an organic material to biohydrogen. Fermentation generally is any process by anaerobic biochemical reactions in which an enzyme (or several enzymes produced by a microorganism) catalyses the conversion of one substance into another.

Fuel cell assembly 19 may include one or both of a hydrogen fuel cell and a microbial fuel cell.

Waste management system 10 is based on the concept that waste streams from one subsystem process can be turned into "fuel" or feedstocks for other subsystem processes. The subsystem technologies are synergistically interlocked through a primary cycle and several secondary cycles such that processes, based on one component subsystem, convert a specific type of waste into a feedstock for processes, based on another technology subsystem, until the recycling loop is closed.

In a primary cycle, the first step is to burn or combust woods and plastics 37 and waste oils 38 in burner 12 to recover thermal energy 40, primarily in the form of steam, which also reduces most of the volume of that solid waste into residual ash 41. Outside air 43 is supplied to burner 12 to support combustion. A portion of the ash from the combustion process is recycled to bioreactor 16 as minerals and biocarriers. Thermal energy 40, mostly as steam, recovered from the combustion process is directed to the saccharification step in hydrothermal processor 14 in which paper and cardboard 35, a primary source of cellulose, are converted into fermentable sugars. The dark fermentation process in bioreactor 16 converts a mixed stream of a saccharification broth 42, food wastes 32 and blackwater 33 into hydrogen 50 and volatile fatty acids (VFAs) 48. Fuel cell assembly 16 produces electrical energy 52 from hydrogen 50 (via hydrogen fuel cells) and from fermentation broth 48 (via microbial fuel cells). Potable water can be reclaimed from fermentation broth 48 by reverse osmosis (RO) and other water purification technologies in water purification assembly 20. Potable water 54 is also a byproduct of operation of the hydrogen fuel cells.

The hydrogen 50 and volatile fatty acids 48 produced in bioreactor 16 are converted to electricity in place by the fuel cells, removing a need to store hydrogen or VFAs. Generated electricity 52 is used within system 10. If excess thermal energy from mobile electricity generators is available, the filtrate (the stream passing through an RO membrane); and/or retentate (the stream rejected by an RO membrane) of the reverse osmosis process can be sterilized. The filtrate water can otherwise be reused for shower, laundry, vehicle washing and dust control, while the retentate water can be removed by surface evaporation in lagoons. A portion of the retentate water can also be returned to hydrothermal processor 14 for sterilization.

Several secondary cycles contribute to effective performance of the primary cycle work and tie up loose ends in terms of material and energy balances. For example, a pH buffering method may be incorporated into the fermentation process, and pH buffer chemicals recovered from the separation and combustion processes and returned back to the fermentation process. Sludge (dewatered microbial cell mass and insoluble hydrocarbon fractions) from the fermentation process can be fed into the saccharification process to be further degraded under hydrothermal conditions. Solids which are not fermentable, such as plastic spoons and forks from unsorted kitchen wastes, can be fed into the combustion process. The electrical energy generated from the fuel cells is used within system 10 to drive motors required in the saccharification, fermentation and water purification processes.

Effective hydrothermal saccharification requires high temperatures to reach the necessary thermodynamic states, particularly temperature and pressure, to promote the saccharification process within a hydrothermal processor. To achieve those necessary thermodynamic states, a steam accumulator, or steam accumulation vessel, 62 is preferably added to system 10 as shown in FIG. 1. The output 44 of steam accumulator 62 is then supplied to hydrothermal processor 14.

Figure 2:
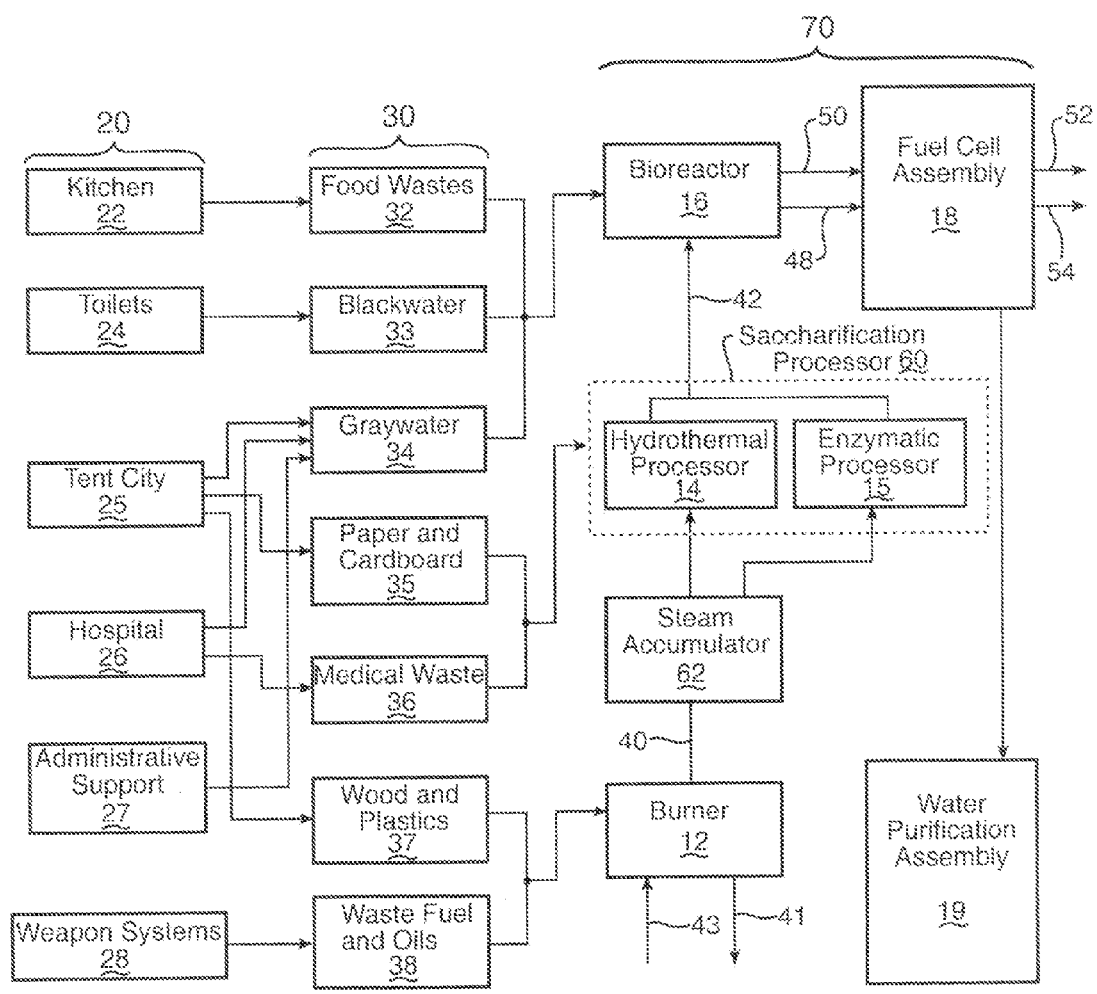
FIG. 2 is another example embodiment showing the addition of enzymatic saccharification to the system of FIG. 1.

The difficulties in achieving effective saccharification using a hydrothermal process may also be improved by adding enzymatic saccharification as indicated by replacing hydrothermal processor 14 with a more broadly termed saccharification processor 60 as part of a waste management and resource recovery system 70 shown in FIG. 2. Saccharification processor 60 includes both hydrothermal saccharification processor 14 and an enzymatic saccharification processor 15.

Reverse osmosis is described in "Reverse Osmosis Processing of Organic Model Compounds and Fermentation Broths," R. A. Diltz, T. V. Marolla, M. V. Henley and L. Li, *Bioresource Technology*, 2007, vol. 98, pp. 686-695, which is incorporated by reference into this description.

The teachings of the present invention will allow maintenance of deployable bases as self-contained operating systems that will leave relatively little trace once the base is disbanded and personnel return home. Use of the present invention will not only reduce operational and environmental costs associated with deployable bases, but also greatly enhance safety for deployed personnel because it does not require any support from external entities such as outside contractors having access to the base.

The present invention is part of ongoing development of the military CONsolidated and Deployable Omni-Recycling (CONDOR) System.

Various modifications to the invention as described may be made, as might occur to one with skill in the art of the invention, within the scope of the claims. Therefore, all contemplated embodiments have not been shown in complete detail. Other embodiments may be developed without departing from the spirit of the invention or from the scope of the claims. For example, mixed microbial populations may be used in the dark fermentation process.

We claim:

1. A waste management and resource recovery system, comprising a plurality of subsystems:
   (a) wherein at least part of the output of each of a subplurality of the subsystems is supplied to at least one other subsystem as an input to that other subsystem;
   (b) wherein the subsystems include:
      (i) a burner;
      (ii) a hydrothermal processor assembly;
         (A) wherein the hydrothermal processor assembly is in communication with the burner;
      (iii) a bioreactor assembly;
         (A) wherein at least part of the output from the hydrothermal processor assembly is an input to the bioreactor assembly; and,
      (iv) a fuel cell assembly;
         (A) wherein at least part of the output from the bioreactor processor assembly is an input to the fuel cell assembly; and,
   (c) further including a steam accumulator for supplying steam from the burner to the hydrothermal processor assembly.

2. A waste management and resource recovery system, comprising a plurality of subsystems:
   (a) wherein at least part of the output of each of a subplurality of the subsystems is supplied to at least one other subsystem as an input to that other subsystem; and,
   (b) wherein the subsystems include:
      (i) a burner;
      (ii) a hydrothermal saccharification processor assembly;
         (A) wherein the hydrothermal saccharification processor assembly is in communication with the burner;
      (iii) a steam accumulator for supplying steam from the burner to the hydrothermal saccharification processor assembly;
      (iv) an enzymatic saccharification processor assembly;
         (A) wherein the enzymatic saccharification processor assembly is in communication with the burner;
      (v) a bioreactor assembly;
         (A) wherein at least part of the outputs from the hydrothermal saccharification processor assembly and the enzymatic saccharification processors are inputs to the bioreactor assembly; and,
      (vi) a fuel cell assembly;
         (A) wherein at least part of the output from the bioreactor assembly is an input to the fuel cell assembly.

* * * * *